United States Patent [19]

Faist et al.

[11] Plant 4,818

[45] Jan. 26, 1982

[54] CALLISSIA PLANT

[76] Inventors: Charles J. Faist, 5313-A Calle Minorca, Sarasota, Fla. 33581; B. George Weich, Summerwood Farms, Corner Border & Jackson Rds., Venice, Fla. 33595

[21] Appl. No.: 153,615

[22] Filed: May 27, 1980

[51] Int. Cl.[3] ..... A01H 5/00

[52] U.S. Cl. ..... Plt./88

[58] Field of Search ..... Plt./88

*Primary Examiner*—James R. Feyrer

*Attorney, Agent, or Firm*—Benjamin P. Reese, II

[57] ABSTRACT

A new and distinct variety of the Callissia family characterized by the pink coloration of leaves and stems. The leaves on each plant are either solid pink in color or variegated with alternating pink and green regions, or both. Upon first seeing the plant, one is given the impression that its stem is covered with small pink flowers. The plant is particularly striking when contrasted with the normal green color of *Callissia repens*.

3 Drawing Figures

BACKGROUND AND SUMMARY OF INVENTION

The present invention relates to a new and distinct variety of the Callissia family which was discovered by the inventors in a greenhouse on their nursery property in the vicinity of Venice, Fla. The new and distinct variety was discovered as a mutation of *Callissia repens* and has been named the *Callissia repens* (cv) Pink Lady by the inventors.

At the time of their discovery, the inventors were commercially growing a block of *Callissia repens* in a greenhouse on their nursery property. In the course of those growing operations, the attention of the inventors was attracted to one particular plant in the block which bore a mutant leaf quite different in appearance from the other leaves on the plant, as well as on all other plants in the block, and unlike the leaves which they had seen on other Callissia varieties. Upon close inspection of this particular plant, the inventors observed that the mutant leaf was variegated. In particular, the mutant leaf was of the green color which is characteristic of Callissia varieties with a plurality of parallel markings of a distinctive pink hue. The appearance of the mutant leaf was particularly striking inasmuch as it had sported and was growing from a stem having normal, solid green *Callissia repens* leaves growing immediately above and below the mutant leaf.

The inventors took immediate steps to preserve the mutation which they had discovered and to keep it under close observation. Shortly after its discovery, a single eye cutting was taken from the mutant leaf and propagated. The results of this initial asexual reproduction of the mutation were very pleasantly surprising. While some of the newly propagated plants had leaves which were essentially identical in appearance to the original mutant leaf, other of the plants had leaves with slightly different patterns of variegation, including variations in the number, size, spacing and hue of the pink markings. Also, some of the plants had leaves which were not variegated at all, but were either the normal, solid green color characteristic of *Callissia repens* or one of several different shades of pink. In general, the solid green leaves were growing from green stems and the solid pink leaves and variegated leaves were growing from pink stems.

The inventors asexually reproduced the plants which they obtained by propagation of the single eye cutting from the original mutant leaf by propagating tip cuttings, including removal and rooting of terminal shoots having three or more leaves, and single eye cuttings. Furthermore, the inventors are using both of these methods to reproduce the progeny of these plants on a continuing basis. After several generations, the inventors have observed that the progeny of plants having solid green leaves have solid green leaves characteristic of *Callissia repens*. On the other hand the progeny of plants having either solid pink leaves or variegated leaves, or both, have either solid pink leaves or variegated leaves, or both.

Continued observation and testing of the progeny of plants having either solid pink leaves or variegated leaves, or both, have convinced the inventors that such plants represent a new and improved variety which is distinctly different from the parent variety, *Callissia repens*. The inventors have observed, however, that while propagation of cuttings from plants having solid pink leaves is possible, it is exceedingly difficult to accomplish. On the other hand, propagation of cuttings from plants having variegated leaves for asexual reproduction of plants having either solid pink leaves or variegated leaves, or both, has proved to be a relatively simple task. For these reasons, the inventors do not routinely attempt to propagate cuttings from plants having solid pink leaves only. Subsequent propagation of the single eye cutting taken from the original mutant leaf, the inventors have not observed any entire plant reversions to the normal, solid green color characteristic of *Callissia repens* for plants propagated from cuttings taken from either a variegated or a solid pink portion of a plant of this new and distinct variety. The new and distinct variety displays leaves having a broad range of pink hues. A *Callissia repens* plant having such characteristics was not previously known to the inventors. The inventors have appropriately named this variety the *Callissia repens* (cv) Pink Lady. The first impression had by most persons who view the plant is that its stem is covered with small pink flowers notwithstanding that the new and improved variety has not produced flowers. This impression is accentuated when plants of *Callissia repens* (cv) Pink Lady are grown interdispersed in a block containing normal solid green *Callissia repens*.

The plant of *Callissia repens* (cv) Pink Lady is a rapid grower. Under normal greenhouse conditions in the vicinity of Venice, Fla., a well developed young plant can be grown from a tip cutting within eight to ten weeks. The plant is vigorous, compact and self-branching. And, it has retained its distinctive characteristics through successive asexual reproduction.

DESCRIPTION OF DRAWINGS

The accompanying drawings serve, by color photographic means, to illustrate the new and distinct plant variety, wherein.

DETAILED PLANT DESCRIPTION

Figure 1:
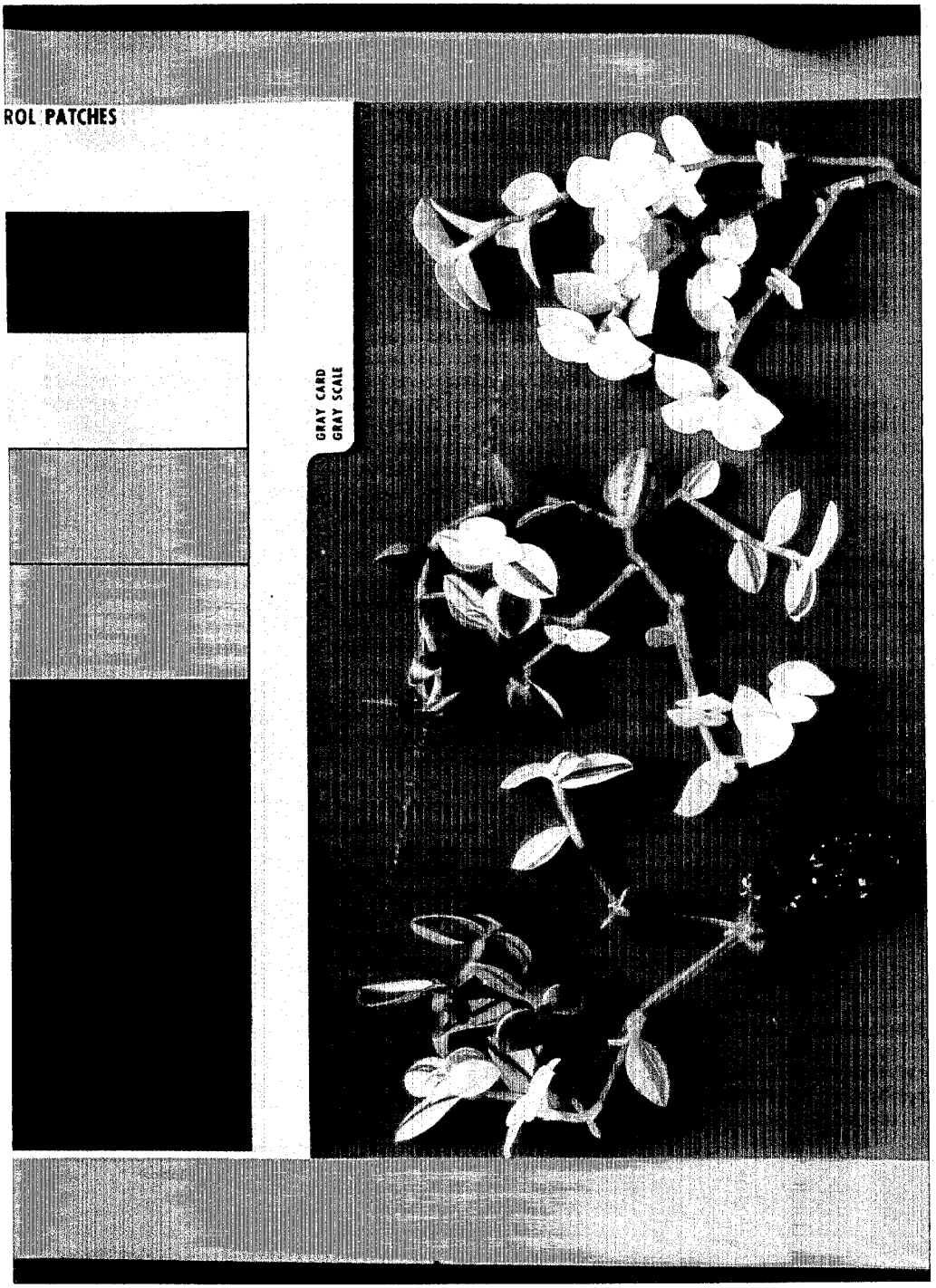
FIG. 1 is a color photograph showing three plants of the new and distinct variety of the present invention, *Callissia repens* (cv) Pink Lady, in close proximity to a Royal Horticultural Society Colour Chart (London, 1966).
Figure 2:
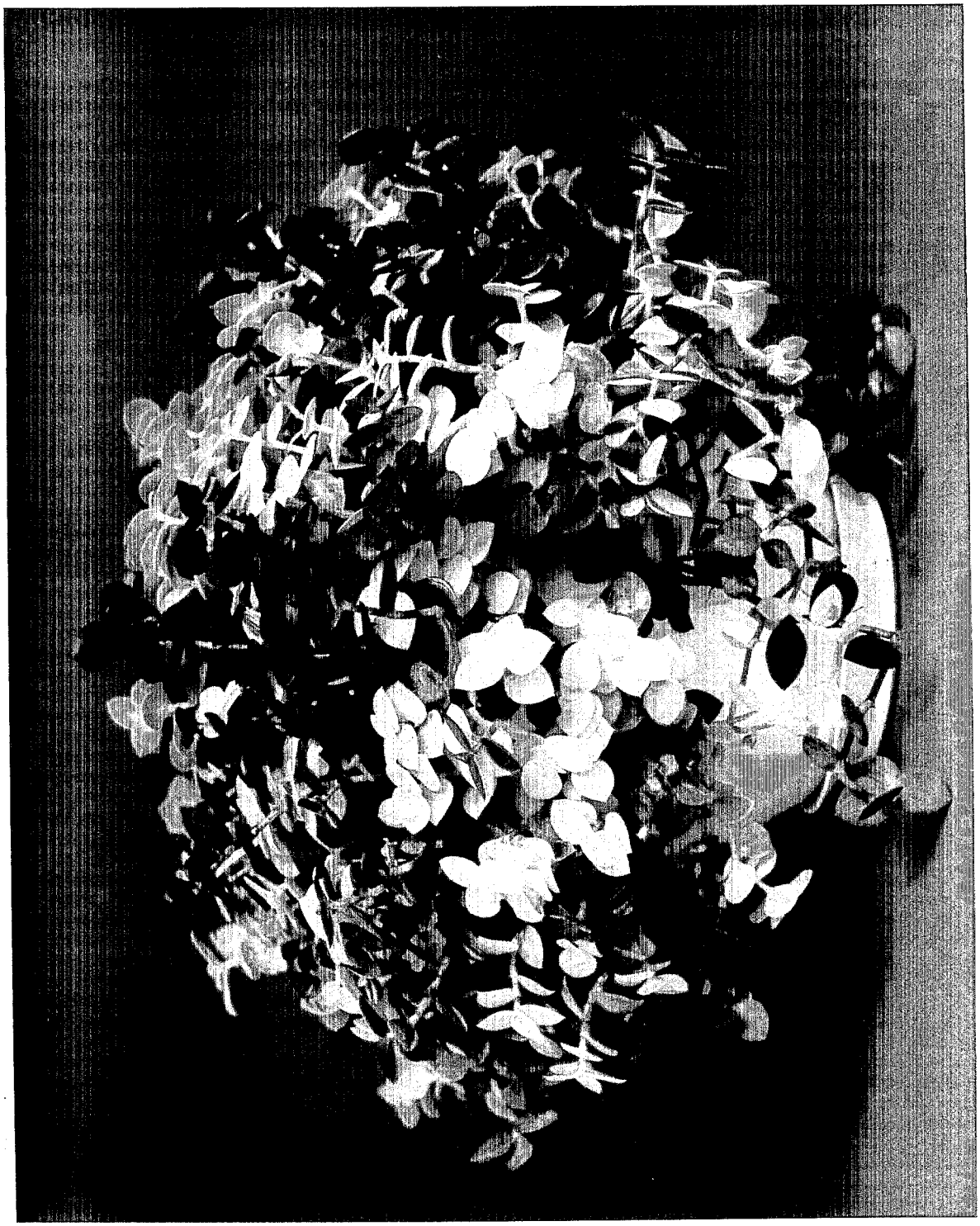
FIG. 2 is a color photograph showing one side of a potted arrangement of growing plants of the *Callissia repens* (cv) Pink Lady variety interdispersed with growing plants of the *Callissia repens* variety.
Figure 3:
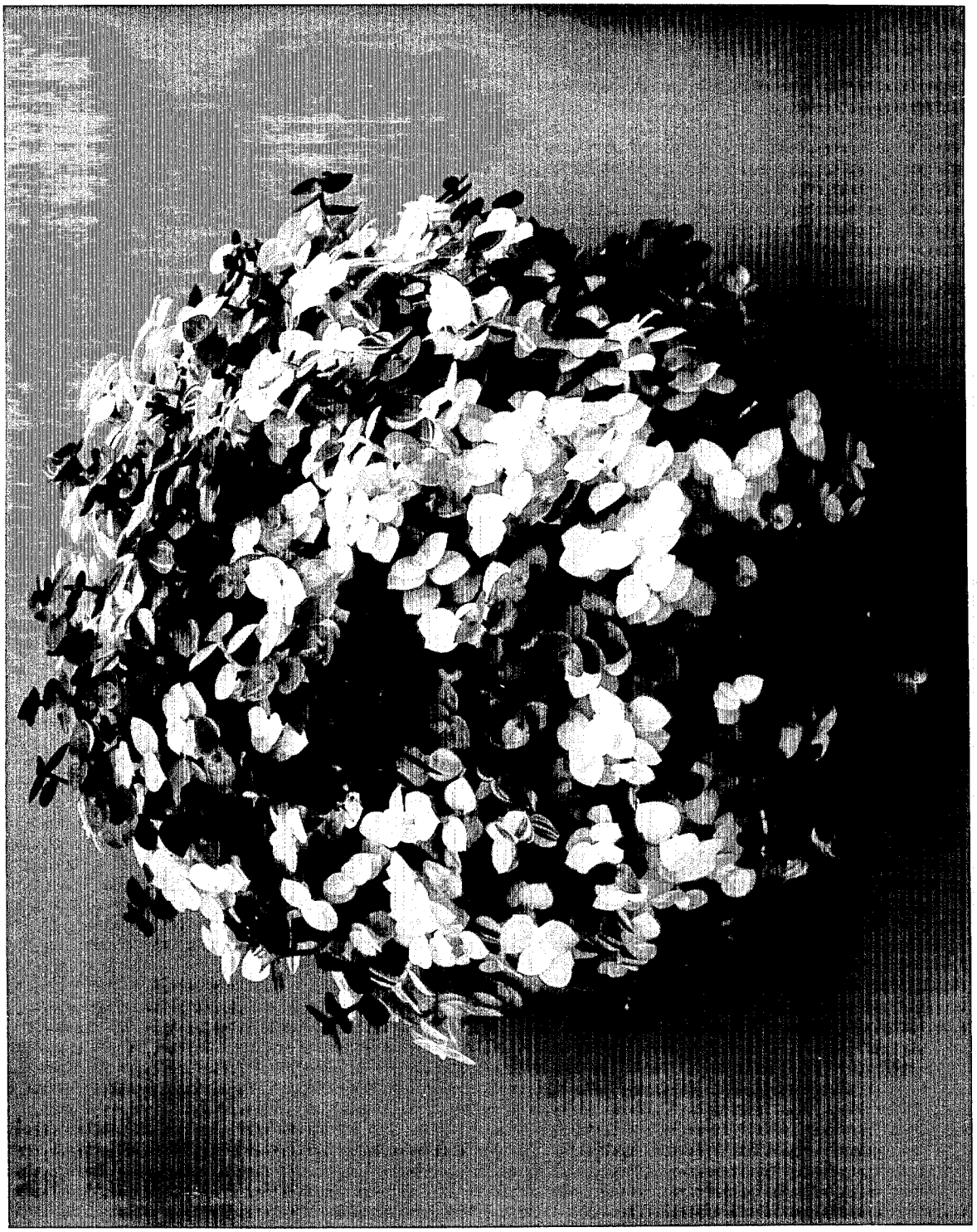
FIG. 3 is a color photograph showing the top of the potted arrangement shown in FIG. 2.

The following is a detailed description of the new and distinct Callissia variety discovered by the inventors, as based on observations under daylight illumination of 1,000 foot-candles of specimen plants grown at their nursery in the vicinity of Venice, Fla., with color terminology in accordance with the Royal Horticultural Society Colour Chart (London, 1966), except where general color terms of ordinary dictionary significance are obvious:

Name: *Callissia repens* (cv) Pink Lady.

Origin: A vegetative leaf mutation on a plant of the *Callissia repens* variety.

Classification:

A. *Botanic.*—Commeliaceae family.
B. *Commercial.*—Foliage plant.
C. *General.*—Herbaceous perennial.

Form: Compact, cascading, as a basket or pot plant. Creeping, sprawling, forming a mat as a ground cover.

Growth: Vigorous, self-branching.

Leaf:

A. *Shape.*—Ovate, acute or acuminate, subcordate at sessile base.
B. *Texture.*—Glabrous, succulent.
C. *Margin.*—Entire.
D. *Arrangement.*—Alternate.
E. *Venation.*—Parallel and obscure.
F. *Attachment.*—Sessile; sheaths, usually glabrous, villous-ciliate.
G. *Size.*—1 cm to 1.5 cm wide, 1 cm to 1.5 cm long.
H. *Color.*—1. General — prominent albino areas which upon exposure to sufficient sunlight (1,000 foot-candles) are in color of red hues and which comprise either the entire leaf or are separated longitudinally by intervening chlorophyllous areas. 2. Albino areas (top) — predominately red group 56A, B. 3. Albino areas (bottom) — predominately red, purple 68B when subjected to 1,000 foot-candles of sunlight for a prolonged period of time. 4. Chlorophyllous areas (top) — green group 137A, B. 5. Chlorophyllous areas (bottom) — similar to the top with diffuse purple striations of the purple-violet group 80A.

Stem:

A. *General.*—Slender, prostrate, elongate.
B. *Texture.*—Succulent, glabrous.
C. *Arrangement.*—Alternate or simple.
D. *Shape.*—Circular in cross section.
E. *Diameter.*—1 mm to 1.5 mm.
F. *Internodal length.*—0.5 cm to 1 cm at 1,000 foot-candles of sunlight.
G. *Color.*—Variable in accordance with leaf albinoism from the red-purple group 72A, B to the greyed-purple group 185A, B at 1,000 foot-candles of sunlight.
H. *Sheaths.*—Glabrous, villous-ciliate, prominent striations of the purple-violet group 80A.

Inforescense: None produced.

We claim:

1. A new and distinct variety of Callissia plant substantially as described and illustrated, characterized particularly as to novelty by its solid pink leaves, variegated leaves and pink stems.

* * * * *